United States Patent [19]

Humber et al.

[11] 4,284,767

[45] Aug. 18, 1981

[54] PROCESS FOR PREPARING 3-CARBAMOYLOXYMETHYL CEPHALOSPORINS

[75] Inventors: David C. Humber, London; Stuart B. Laing, Harrow; Gordon G. Weingarten, London, all of England

[73] Assignee: Glaxo Group Limited, London, England

[21] Appl. No.: 112,201

[22] Filed: Jan. 15, 1980

Related U.S. Application Data

[63] Continuation of Ser. No. 27,804, Apr. 6, 1979, abandoned.

[30] Foreign Application Priority Data

Apr. 7, 1978 [GB] United Kingdom ............... 13799/78

[51] Int. Cl.$^3$ ........................................... C07D 501/04
[52] U.S. Cl. ....................................... 544/22; 544/16; 544/21
[58] Field of Search ............................. 544/21, 22, 16

[56] References Cited

U.S. PATENT DOCUMENTS

| | | | |
|---|---|---|---|
| 3,355,452 | 11/1967 | Urech et al. | 544/16 |
| 3,875,152 | 4/1975 | Sellstedt | 544/28 |
| 3,905,967 | 9/1975 | Webber | 544/22 |
| 4,043,991 | 8/1975 | Hamma et al. | 544/21 |

OTHER PUBLICATIONS

Lapidot et al., J. Chem. Soc., (1958), pp. 1713–1717.
Shokol et al., Chemical Abstracts, vol. 73, 14927b (1970).
Cotton et al., Advanced Inorganic Chemistray, (1967), pp. 506–508.

*Primary Examiner*—Paul M. Coughlan, Jr.
*Attorney, Agent, or Firm*—Bacon & Thomas

[57] ABSTRACT

A process for the preparation of a 3-carbamoyloxymethyl cephalosporin compound which comprises reacting a 3-hydroxymethyl cephalosporin with dihalophosphinyl isocyanate and converting the resulting 3-phosphonocarbamoyloxymethyl cephalosporin reaction product by hydrolysis to the desired compound. The isocyanates used in the process are readily available and easy to handle and thus the process avoids the use of hazardous and/or expensive reagents.

4 Claims, No Drawings

PROCESS FOR PREPARING 3-CARBAMOYLOXYMETHYL CEPHALOSPORINS

This is a continuation of application Ser. No. 27,804 filed Apr. 6, 1979, now abandoned.

This invention is concerned with the preparation of cephalosporin compounds substituted at the 3-position by a carbamoyloxymethyl group.

The cephalosporin compounds in this specification are systematically named with reference to "cepham" after J. Amer. Chem. Soc., 1962, 84, 3400; the term "cepham" refers to the basic cepham structure with one double bond.

Many cephalosporin compounds possessing a degree of antibacterial activity are known in the art. These compounds possess $\Delta^3$ unsaturation and are ordinarily substituted at the 3-position by a methyl or substituted methyl group, at the 4-position by a carboxy group, and at the $7\beta$-position by an acylamido group. In some instances the compounds may additionally be substituted at other positions, for example at the 2-position (e.g. by one or two methyl groups or a methylene group) and/or at the $7\alpha$-position (e.g. by a lower alkyl, alkoxy or alkylthio group).

One class of cephalosporin antibiotics which has attracted considerable interest comprises compounds substituted at the 3-position by a carbamoyloxymethyl group, i.e. the group $-CH_2.O.CO.NH_2$; a number of antibiotics of this type, possessing a variety of $7\beta$-acylamido groups, have been proposed.

These 3-carbamoyloxymethyl cephalosporin compounds may usefully be prepared by reacting a 3-hydroxymethyl cephalosporin compound with a substituted isocyanate, i.e. a compound of formula

R.NCO        (I)

where R is a labile protecting group, e.g. a trichloroacetyl, 2,2,2-trichloroethoxycarbonyl or chlorosulphonyl group. This reaction leads to formation of an N-monosubstituted 3-carbamoyloxymethyl cephalosporin wherein the 3-position substituent has the formula $-CH_2.O.CO.NHR$ where R is as defined above; the labile group R may be cleaved from this product by, for example, hydrolytic, reductive or acid-induced cleavage as appropriate, to yield the desired 3-carbamoyloxymethyl cephalosporin.

A disadvantage of previously proposed processes of the above type is that the isocyanates of formula (I) which have hitherto been suggested as appropriate carbamoylating agents tend to be somewhat difficult or inconvenient to prepare, for example involving hazardous and/or expensive reagents. Moreover these reagents and the resulting isocyanates may be difficult or impossible to transport. Thus, for example, the preparations of carbamoylating agents such as chlorosulphonyl isocyanate and trichloroacetyl isocyanate typically involve reaction of sulphur trioxide with cyanogen chloride and trichloroacetamide with oxalyl chloride respectively.

We have now discovered that 3-carbamoyloxymethyl cephalosporins may be prepared in high yield by reaction of 3-hydroxymethyl cephalosporins with dihalophosphinyl isocyanates, i.e. compounds of formula $X_2.PO.NCO$, where each X represents a halogen atom, such as chlorine. Such isocyanates may be prepared in relatively simple and economic manner, if desired without isolation. The novel N-monosubstituted 3-carbamoyloxymethyl cephalosporin intermediates initially formed in this reaction may readily be converted to the desired N-unsubstituted analogue.

Thus according to one aspect of the present invention there is provided a process for the preparation of a 3-carbamoyloxymethyl cephalosporin compound which comprises reacting a 3-hydroxymethyl cephalosporin compound with a dihalophosphinyl isocyanate and converting the resulting cephalosporin reaction product to a 3-carbamoyloxymethyl cephalosporin.

3-Hydroxymethyl cephalosporin compounds which may be used as starting materials include compounds of the formula

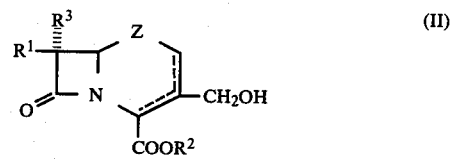
(II)

[wherein $R^1$ represents a protected amino group (e.g. an acylamido group, conveniently one which contains 1–40 e.g. 1–20, carbon atoms, or a precursor therefor); $R^2$ represents hydrogen or a carboxyl blocking group (e.g. the ester-forming residue of an alcohol, phenol, silanol or stannanol, the residue preferably being one which may readily be split off at a later stage); $R^3$ represents hydrogen or a lower (e.g. $C_{1-4}$) alkyl, alkythio or alkoxy group e.g. a methoxy group; Z is $>S$ or $>S\rightarrow O$ ($\alpha$- or $\beta$-); and the dotted line bridging the 2-, 3- and 4-positions of the molecule indicates that the compounds may be ceph-2-em or ceph-3-em compounds] and, where appropriate, salts (e.g. alkali metal such as sodium or potassium, alkaline earth metal such as calcium, ammonium and organic amine salts) thereof.

The 3-carbamoyloxymethyl cephalosporin final products may be represented by the formula

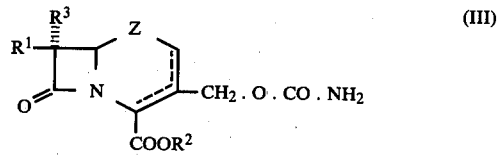
(III)

(wherein $R^1$, $R^2$, $R^3$, Z and the dotted line have the above defined meanings).

While not wishing to be bound by any theoretical considerations we have found that the process according to the invention generally proceeds in three stages. In a first stage, the 3-hydroxymethyl group of the cephalosporin starting material reacts with the dihalophosphinyl isocyanate to form a 3-dihalophosphorylcarbamoyloxymethyl (or "dihalophosphinylcarbamoyloxymethyl") group. This group then undergoes hydrolysis in a second stage to form a corresponding 3-phosphonocarbamoyloxymethyl (or "dihydroxyphosphorylcarbamoyloxymethyl") cephalosporin, which itself undergoes further hydrolysis in a third stage to give the desired product. The process is generally performed without isolation of any intermediate compounds.

It should be appreciated that formulae (II) and (III) are skeletal formulae and are intended to embrace closely related analogues such as 2-methyl, 2-methylene and 2,2-dimethyl cephalosporins.

A particularly preferred product of the process according to the invention containing an (α-etherified oximino)-acylamido group in the 7-position is (6R,7R)-3-carbamoyloxymethyl-7-[Z-2-(fur-2-yl)-2-methoxyiminoacetamido]ceph-3-em-4-carboxylic acid and non-toxic derivatives thereof, the acid having the approved name cefuroxime and which has been found to be a valuable broad spectrum antibiotic.

Salts, particularly non-toxic salts, of the compounds of formula (III) may be formed in any convenient way, for example according to methods well known in the art. Salt formation may take place without prior isolation of the corresponding acid, by reaction with a suitable reagent e.g. an alkali metal bicarbonate or 2-ethylhexanoate.

The dihalophosphinyl isocyanate used in the process according to the invention is conveniently dichlorophosphinyl isocyanate by virtue of its ready availability.

It is convenient to employ substantially equimolar amounts of the 3-hydroxymethyl cephalosporin and the dihalophosphinyl isocyanate; the use of a small excess (e.g. up to 0.5 moles) of dihalophosphinyl isocyanate may, however, be advantageous to allow for side reactions between this reagent and hydroxylic impurities (e.g. water) in the reaction system. In view of the susceptibility of dihalophosphinyl isocyanates to reaction with water, the reaction with the 3-hydroxymethyl cephalosporin is desirably conducted under anhydrous conditions; thus, for example, the reactions may be carried out under an appropriate desiccant or the reaction system may be kept dry by passage of a stream of an anhydrous inert gas such as nitrogen.

The reaction of the 3-hydroxymethyl cephalosporin compound with the dihalophosphinyl isocyanate is conveniently carried out in solution, for example, in a substantially inert organic solvent, since this facilitates control of reaction conditions such as temperature. Solvents which may be used include chlorinated hydrocarbons such as methylene chloride or 1,2-dichloroethane; ethers such as tetrahydrofuran, dioxan or diethylene glycol dimethyl ether (diglyme); esters such as ethyl acetate; ketones such as acetone and hydrocarbons such as benzene or cyclohexane. Mixtures of solvents, e.g. comprising two or more of the above-described solvents, may also be used. As indicated above, the solvent should desirably be substantially free from hydroxylic impurities to avoid unwanted side reactions involving the dihalophosphinyl isocyanate.

The temperature employed in the reaction of the 3-hydroxymethyl cephalosporin and dihalophosphinyl isocyanate may vary depending on the solvent used, but may, for example, be in the range −50° to +105° C., e.g. −20° to +50° C. The reaction is exothermic, so that cooling of the reaction system may be desirable in order to maintain a steady temperature.

The 3-hydroxymethyl cephalosporin and dihalophosphinyl isocyanate may be brought together in any convenient manner. Preferably a solution or suspension of the 3-hydroxymethyl cephalosporin may be added to the dihalophosphinyl isocyanate or a solution thereof. The dihalophosphinyl isocyanate may conveniently be formed without isolation as described in greater detail hereinafter.

The reaction may be monitored by, for example, chromatography, e.g. to determine the degree of consumption of the 3-hydroxymethyl cephalosporin.

Conversion of the 3-dihalophosphorylcarbamoyloxymethyl cephalosporin intermediate to the cephalosporin of formula (III) may be initiated by reaction with water e.g. by addition of the reaction system to water. As indicated above, the hydrolysis to a compound of formula (III) is believed to be a multistep process. The first stage is conveniently conducted at a pH of 10 or less, e.g. 2.5 to 6. However, if it is desired to isolate any intermediate the hydrolysis is desirably effected at a pH of from 5 to 10, preferably 7 to 9. Since the hydrolysis in the first stage is accompanied by the formation of hydrohalic acid it may be desirable to add a base to act as an acid binder. This may particularly be the case if the intermediate produced is insoluble at a low pH or if the cephalosporin contains any acid-susceptible groups.

In the second hydrolysis stage the pH should generally be kept below pH 5 and preferably in the range pH 3 to 4. In order to work in this range it may be appropriate to add either acid or base to the reaction mixture. In the hydrolysis reactions, it may be desirable to buffer the aqueous system, e.g. with sodium carbonate, sodium hydrogen carbonate, sodium acetate, sodium phosphate, calcium carbonate or calcium hydroxide, or add an acid or base such as sodium hydroxide during the course of the hydrolyses, in order to maintain the pH within the desired limits. If it is desired to isolate an intermediate it is generally important that the pH of the hydrolysis is not allowed to fall below values of about 5. The use of aqueous sodium hydrogen carbonate in this way has proved particularly convenient when effecting hydrolysis.

The hydrolyses may, for example, be conducted at a temperature in the range −5° to +105° C., e.g. +15° to +60° C., and may, where necessary, be monitored by, for example, chromatography. The reaction time is significantly affected by both the temperature and pH of the system; thus, for example, in preparing compounds of formula (III) times of 3 to 5 hours are typically required at 40° C. and pH 3 to 5, times of about 1 to 2 hours are typically required at 55° C. and pH 3 to 6, while times of 20 to 30 hours or more may be required at room temperature and pH 3 to 6.

After completion of the hydrolyses and any necessary purification steps the desired 3-carbamoyloxymethyl cephalosporin (III) may be isolated by, for example, conventional methods, e.g. by solvent extraction where the cephalosporin compound is a carboxyl protected derivative such as an ester or by acidification and precipitation or extraction where the cephalosporin compound is a free acid or a salt.

The dihalophosphinyl isocyanate employed in the process of the invention may readily be prepared by, for example, reaction of the appropriate phosphorus pentahalide, e.g. phosphorus pentachloride, with a carbamic acid ester, for example a lower alkyl carbamate (unless otherwise stated, the qualification "lower" is used in this specification to designate a group containing up to 8, e.g. 1 to 6 carbon atoms). The use of methyl carbamate is of particular advantage as this is an inexpensive reagent which is commercially available. The reaction may conveniently be accomplished by mixing the reagents in the presence of a diluent, e.g. dioxan, methylene chloride or 1,2-dichloroethane, and is accompanied by the formation of hydrogen halide and alkyl halide. When phosphorus pentachloride is employed as the phosphorus pentahalide this may if desired be formed in situ by interacting phosphorus trichloride and chlorine, if desired in the presence of a diluent.

Crude dihalophosphinyl isocyanates prepared by techniques such as those described above may conveniently be reacted directly, without distillation, with the 3-hydroxymethyl cephalosporin; in such cases it may be advantageous to ensure substantially complete removal of hydrogen halide from the crude dihalophosphinyl isocyanate, since the presence of hydrogen halide during carbamoylation may promote such undesirable side reactions as lactonisation of the 3-hydroxymethyl cephalosporin.

Acylamido groups which may be present at the 7-position of cephalosporin starting materials and products in the process of the invention [e.g. as the group $R^1$ in formulae (II) and (III)] may, for example, be selected from the wide range of side chain acylamido groups known in the β-lactam antibiotic art. It will be appreciated that where the acylamido group carries substituents such as amino, hydroxy or mercapto groups which are susceptible to reaction with dihalophosphinyl isocyanates, these substituents should be protected by substitution with an appropriate group unless such further reaction is desired in a particular instance. Thus, for example, amino groups may be protected by substitution with a mono- or divalent blocking group, suitable groups including acyl groups, for example lower alkanoyl such as acetyl, substituted lower alkanoyl, e.g. lower haloalkanoyl such as phenylacetyl and aroyl such as benzoyl or phthaleyl; lower alkoxycarbonyl groups such as ethoxycarbonyl, isobutyloxycarbonyl or t-butoxycarbonyl and substituted lower alkoxycarbonyl groups e.g. lower haloalkoxycarbonyl such as 2,2,2-trichloroethoxycarbonyl; aryl-lower alkoxycarbony groups such as benzyloxycarbonyl; sulphonyl groups, for example lower alkylsulphonyl such as methanesulphonyl and arylsulphonyl such as benzene sulphony or p-toluene sulphonyl; ylidine groups formed by reaction with an aldehyde or ketone which forms a Schiff's base, for example acetone, methylethylketone, benzaldehyde, salicylaldehyde or ethyl acetoacetate; and divalent groups such that the nitrogen atom forms part of a dihydropyridine ring (protecting groups of this last sort being obtained by, for example, reaction with formaldehyde and a β-ketoester, e.g. acetoacetic ester, as described in our Belgian Pat. No. 771,694). Hydroxyl and mercapto groups may for example, be protected by substitution with carboxylic or sulphonic acyl groups in like manner to amino groups, or, where appropriate, by etherification or thioetherification (e.g. to introduce a branched lower alkyl group such as isopropyl or t-butyl or an aralkyl group such as benzyl, benzyl substituted by one or more methoxy groups, diphenylmethyl or triphenylmethyl). The protecting groups may subsequently be removed from the cephalosporin product by methods well known in the art, for example by hydrolytic, reductive or acid-induced cleavage as appropriate.

Where the acylamido group is substituted by a carboxyl group it may also be advantageous to protect this during the course of the reaction, for example by etherification to introduce an ester group as herein described in connection with the group $R^2$.

Specific acyl groups which may be present in acylamido groups $R^1$ are illustrated in the following list, which is not intended to be exhaustive:-

(i) $R^uC_nH_{2n}CO-$ where $R^u$ is aryl (carbocyclic or heterocyclic), cycloalkyl, substituted aryl, substituted cycloalkyl, cycloalkadienyl, or a non-aromatic or mesionic group, and n is an integer from 1 to 4. Examples of this group include phenylacetyl wherein the phenyl group may if desired be substituted by, for example, one or more of fluoro, nitro, protected amino, protected hydroxy (e.g. esterified hyroxy such as acetoxy), methoxy, methylthio or methyl; N,N,-bis (2-chloroethyl) aminophenylpropionyl; thien-2- and -3-ylacetyl; 3- and 4-isoxazolylacetyl either substituted or unsubstituted; pyridylacetyl; tetrazolylacetyl; cyclohexadienylacetyl; or a sydnoneacetyl group. Where n is other than 0, especially where n is 1, the α-carbon atom of the acyl group may be substituted by, for example, an esterified hydroxy (e.g. acyloxy such as formyloxy or lower alkanoyloxy), etherified hydroxy (e.g. methoxy), protected amino (e.g. as hereinbefore described), carboxy, esterified carboxy, triazolyl, tetrazolyl or cyano group or a halogen atom; examples of such α-substituted acyl groups include esterified 2-hydroxy-2-phenylacetyl, N-blocked 2-amino-2-phenyl-acetyl, 2-carboxy-2-phenylacetyl and esterified 2-carboxy-2-phenylacetyl.

(ii) $C_nH_{2n+1}CO-$ where n is 0 or an integer from 1 to 7. The alkyl group may be straight or branched and, if desired may be interrupted by an oxygen or sulphur atom and/or may be substituted by, for example, a cyano group, a carboxy or esterified carboxy group (e.g. an alkoxycarbonyl group), an esterified hydroxy group, a blocked amino group or a carboxycarbonyl (—CO.COOH) or esterified carboxycarbonyl group. Examples of such groups include formyl, cyanoacetyl, butylthioacetyl, hexanoyl, heptanoyl, octanoyl, glutaroyl, esterified glutaroyl, and N-blocked (e.g. N-ethoxycarbonyl or N-benzoyl) and optionally esterified R-5-amino-5-carboxypentanoyl (e.g. R-5-benzamido-5-diphenylmethoxycarbonylpentanoyl or R-5-diphenyl methoxycarbonyl-5-isobutoxycarbonylaminopentanoyl).

where $R^u$ has the meaning defined under (i) and in addition may be benzyl, $R^v$ and $R^w$ (which may be the same or different) each represents hydrogen, phenyl, benzyl, phenethyl or lower alkyl and Z is an oxygen or sulphur atom. Examples of such groups include phenoxyacetyl, 2-phenoxy-2-phenylacetyl, phenoxypropionyl, 2-phenoxybutyryl, benzyloxycarbonyl, 2-phenoxypropionyl, 2-phenoxybutyryl, methylthio phenoxyacetyl, phenylthioacetyl, chloro- and fluoro phenylthioacetyl, pyridylthioacetyl and benzylthioacetyl.

(iv) Substituted glyoxylyl groups of the formula $R^y$.-CO.CO— where $R^y$ is an aliphatic, araliphatic or aromatic group, e.g. phenyl, thienyl or furyl or a fused benzene ring. Also included in this class are the α-carbonyl derivatives of the above substituted glyoxylyl groups, e.g. the α-alkoxyimine, α-aryloxyimino and α-akyloxyimino derivatives, especially those possessing the syn-configuration with respect to the 7-carboxamido group. Groups of this type, of which an example is the Z-2-(fur-2-yl)-2-methoxyiminoacetyl group, and which may be represented by the formula

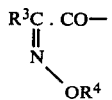

[wherein R³ represents hydrogen or an organic group (especially a carbocyclic or heterocyclic aromatic group such as phenyl, naphthyl, thienyl, thiazolyl e.g. aminothiazolyl, or furyl) and R⁴ represents hydrogen, an acyl group (e.g. a lower alkanoyl, alkenoyl, alkynoyl, haloalkanoyl, alkoxycarbonyl, haloalkoxycarbonyl, alkylthiocarbonyl or aralkyloxycarbonyl group or an aroyl or carbamoyl group) or an etherifying group (e.g. a lower alkyl, alkenyl, alkynyl, cycloalkyl, cycloalkenyl or aralkyl group or a carbocyclic or a heterocyclic aryl group, or any of these groups substituted by a carboxy, esterified carboxy, aminocarbonyl or N-substituted aminocarbonyl group)], are described in greater detail in Belgian Pat. Nos. 778 630; 783 449; 801 997; 806 450; 823 651 and 843 152.

Where R² in formulae (II) and (III) represents an esterifying group this may, for example, be selected from the wide range of esterifying groups known in the cephalosporin art. A range of groups of this type, together with methods for their introduction and subsequent removal, are described in British Pat. No. 1,342,241. Representative esterifying groups thus include aryl lower alkyl groups such as p-methoxybenzyl, p-nitrobenzyl and diphenylmethyl; lower alkyl groups such as t-butyl; and lower haloalkyl groups such as 2,2,2-trichloroethyl. It will of course be appreciated that R² may represent an ester group in a compound which is to be used in medicine in which case this group should be physiologically acceptable. When such an ester group is employed it may not be necessary or desirable to effect deprotection of the carboxyl group.

Where at the end of a given preparative sequence the sulphoxide analogue of the compound of formula (III) or (IV) is obtained, conversion to the corresponding sulphide may, for example, be effected by reduction of the corresponding acyloxysulphonium or alkyloxysulphonium salt prepared in situ by a known method, such as is described in British Patent No. 1453049.

As also described in British Pat. No. 1453049 a ceph-2-em-4-carboxylic ester may be converted into a desired ceph-3-em compound by treatment of the former with a base.

The following Examples serve to illustrate the invention. All temperatures are in °C. The melting point given in Example 2 was determined in an openended capillary tube on a Mettler apparatus and is uncorrected. The melting points given in Examples 8, 9 and 12 were observed on a Mettler apparatus and are given in the form My$^x$ where x is the rate of heating in °C. per minute and y is the insertion temperature. Thin layer chromatography (TLC) using Merck Kieselgel 60 F$_{254}$ plates, run in the solvent systems indicated; detection of spots was by spraying with ninhydrin in n-butanol and heating, or by exposure to iodine vapours, or by irradiation with ultra-violet light at 254 nm. Dry solvents were used and usually contained less than 0.1% (w/v) water; the starting cephalosporins were, if necessary, dried in vacuo at 40°–50° C. and usually contained less than 1% water. The ultraviolet spectra were run in pH 6 phosphate buffer, unless otherwise specified. High pressure liquid chromatography (HPLC) was performed in a 15 cm column packed with Hyperfil FAF silica; the mobile phase was usually 20% methanol/0.05 molar aqueous ammonium dihydrogen phosphate; the u.v. detector was set at the λmax of the desired product and the relative proportions of components were determined by measuring the relative absorption peak areas.

The following abbreviations have been employed in the Examples:

(6R,7R)-3-carbamoyloxymethyl-7-[Z-2-(fur-2-yl)-2-methoxyiminoacetamido]ceph-3-em-4-carboxylic acid is represented as cefuroxime and the corresponding sodium salt as cefuroxime sodium; sodium hydrogen carbonate as NaHCO$_3$; magnesium sulphate as MgSO$_4$; phosphorus pentachloride as PCl$_5$; tetrahydrofuran as THF; and dimethyl sulphoxide as DMSO.

EXAMPLE 1

Cefuroxime

A solution of (6R,7R)-7-[Z-2-(fur-2-yl)-2-methoxyiminoacetamido]-3-hydroxymethylceph-3-em-4-carboxylic acid (3.81 g) in dioxan (50 ml) was stirred with dichlorophosphinyl isocyanate (2.4 g) for 5 minutes.

The reaction mixture was thereafter treated with 3% aqueous NaHCO$_3$ solution (148 ml) and water (2 ml), the temperature being maintained at ca 40° for 5.25 hours and the pH being maintained at 5.0 by the addition of concentrated hydrochloric acid when necessary. The pH was then raised to 6 by addition of saturated NaHCO$_3$ solution and the aqueous solution was extracted with ethyl acetate (200 ml). The aqueous phase was acidified to pH2 using concentrated hydrochloric acid and extracted with ethyl acetate (2×100 ml). The extract was dried (MgSO$_4$) and evaporated to dryness to yield the title compound (3.67 g, 86.5%) as an off-white solid, $[\alpha]_D^{20}$+52.3° (c 1.03, DMSO); $\lambda_{max}$ 274 nm (E$_{1cm}^{1\%}$ 423); purity by HPLC 96%.

EXAMPLE 2

Diphenylmethyl (6R,7R)-3-carbamoyloxymethyl-7-[2-(thien2-yl) acetamido]ceph-3-em-4-carboxylate A stirred solution of diphenylmethyl (6R,7R)-3-hydroxymethyl-7-[2-(thien-2-yl)-acetamido]ceph-3-em-4-carboxylate (5.21 g) in dioxan (50 ml) was treated with dichlorophosphinyl isocyanate (2.4 g) for 5 minutes.

Addition of 3% aqueous NaHCO$_3$ (100 ml) to the stirred solution caused crystallisation of a large amount of solid which was re-dissolved by addition of dioxan (100 ml). The pH of the solution was adjusted to 3 by the addition of 3% aqueous NaHCO$_3$ solution (10 ml) and the solution was maintained at ca 40° for 3 hours, whereupon T.l.E. (chloroform:acetate=3:1) indicated that the reaction was complete.

The reaction mixture was extracted twice with ethyl acetate (200 ml and 100 ml respectively), and the combined organic extracts were washed with saturated NaHCO$_3$ solution (50 ml), water (50 ml), brine (2×50 ml), dried (MgSO$_4$) and evaporated in vacuo to yield a glassy yellow solid (5.99 g). Trituration with ethanol gave the title compound (5.21 g, 92.5%) as a white solid, m.p. 207.6°; $[\alpha]_D^{20}$+40.9° (c 1.0, DMSO).

EXAMPLE 3

Cefuroxime

Dichlorophosphinyl isocyanate (1.46 ml) was added to a stirred suspension of (6R,7R)-7-[Z-2-(fur-2-yl)-2- methoxyiminoacetamido]-3-hydroxymethylceph-3-em-4-carboxylic acid (3.81 g) in acetonitrile (50 ml) cooled to 5°. The reaction mixture was stirred at 5° for 15 minutes and then added to a solution of NaHCO$_3$ (5.1 g) in water (100 ml). This mixture was stirred for 10 minutes when the pH was adjusted from 7.4 to 5.0 with hydrochloric acid. The pH fell to 3.0 after a further 10 minutes so it was readjusted to 5.0 with aqueous sodium hydroxide solution. The mixture was kept at ca. 20° overnight and then heated at 45° for 2 hours when TLC (chloroform:methanol:acetic acid=9:2:1) showed that reaction was essentially complete. The precipitated white solid was removed by filtration and the filtrate was washed with ethyl acetate. The aqueous phase was acidified to pH 1.9 with dilute hydrochloric acid in the presence of ethyl acetate. The aqueous phase was re-extracted with ethyl acetate, and the combined ethyl acetate extracts were washed with 25% aqueous sodium chloride solution and then evaporated. The solid residue was triturated with diethyl ether to give the title compound (3.18 g, 75.0%), purity by HPLC 95.4% and by TLC 91%.

EXAMPLE 4

Cefuroxime

The process of Example 3 was repeated, using dichlorophosphinyl isocyanate (1.46 ml) and a solution of (6R,7R)-7-[Z-2-(fur-2-yl)-2-methoxyiminoacetamido]-3hydroxymethylceph-3-em-4-carboxylic acid (3.81 g) in acetone (50 ml) cooled to 4°, but the reaction mixture was heated at 45° for 2 hours and then kept at 20° overnight, to give the title compound (2.40 g, 56.7%); purity by HPLC 95.6% and by TLC 94.5%.

EXAMPLE 5

Cefuroxime

Dichlorophosphinyl isocyanate (1.46 ml,) was added to a solution of (6R,7R)-7-[Z-2-(fur-2-yl)-2-methoxyiminoacetamido]-3-hydroxymethylceph-3-em-4-carboxylic acid (3.81 g) in THF (50 ml) at 22°, the temperature rising to 31°. The reaction mixture was stirred for 15 minutes and then added to a solution of sodium acetate (5.72 g) in water (50 ml). More sodium acetate (1.64 g) was added over 10 minutes to give a stable pH of 4.6. This solution was stirred at 30° for 1 hour and then heated at 45° for 3.5 hours when TLC (as Example 3) showed the reaction to be complete. The solution, pH 4.6, was clarified by filtration, adjusted to pH 7.0 with aqueous NaHCO$_3$ solution and washed twice with ethyl acetate. The aqueous phase was stirred and acidified to pH 1.9 with dilute hydrochloric acid to precipitate the title compound (2.80 g, 66.0%); purity by HPLC 95.8% and by TLC 96%.

EXAMPLE 6

Cefuroxime

A solution of (6R,7R)-7-[Z-2-(fur-2-yl)-2-methoxyiminoacetamido]-3-hydroxymethylceph-3-em-4-carboxylic acid (3.81 g) in dioxan (20 ml) was added over ca. 1 minute to a stirred solution of dichlorophosphinyl isocyanate (1.46 ml) in 1,2-dichloroethane (30 ml) at 19°, the temperature rising to 28°. The resulting solution was stirred for 15 minutes and then added to a solution of NaHCO$_3$ (5.1 g) in water (70 ml). This mixture was stirred at ca. 30° for 1 hour, and then heated at 40° to 45° for a total of 4.5 hours, the pH being adjusted to 5.0 with hydrochloric acid after 3 hours. The two-phase mixture was adjusted from pH 5.8 to 7.0 with aqueous NaHCO$_3$ solution and the aqueous phase was washed with 1,2-dichloroethane (20 ml) and ethyl acetate (50 ml), and acidified to pH 1.9 with dilute hydrochloric acid in the presence of ethyl acetate. The aqueous phase was re-extracted with ethyl acetate, and the combined ethyl acetate extract washed with 25% aqueous sodium chloride solution and evaporated. The solid residue was slurried with diethyl ether to give the title compound (3.18 g, 75.0%); purity by HPLC 91.6% and by TLC 89.5%.

EXAMPLE 7

Cefuroxime Sodium (6R,7R)-7-[Z-2-(Fur-2-yl)-2-methoxyiminoacetamido]3-hydroxymethylceph-3-em-4-carboxylic acid (19.07 g) was rinsed with ethyl acetate (25 ml) into a stirred solution of dichlorophosphinyl isocyanate (7.35 ml) in ethyl acetate (100 ml) precooled to −5°. This mixture was stirred at 0° for 45 minutes and the resulting solution was added to a stirred solution of NaHCO$_3$ (27 g) in water (270 ml) at 45°. After ca. 10 minutes the pH was adjusted to 3.0 with concentrated hydrochloric acid. The mixture was stirred at 45° for a further 4 hours, the pH being controlled in the range 2.8 to 3.2 by the addition of hydrochloric acid. Acetone (100 ml) was added and the pH was adjusted to 2.0 with hydrochloric acid. The two-phase mixture was filtered and the aqueous phase was extracted with ethyl acetate (100 ml). The combined organic phases were washed with brine (200 ml) and then stirred with charcoal (2 g) for 30 minutes. The charcoal was removed by filtration through kieselguhr and the filter bed was washed with a mixture of acetone (20 ml) and ethyl acetate (20 ml). The combined filtrate and wash were stirred while a 10% solution of sodium 2-ethylhexanoate in acetone was added over 18 minutes to adjust the pH of the resulting suspension to 7.0. The suspension was stirred for 10 minutes and filtered to give the title compound (18.83 g, 81.1%) containing 3.9% water; $[\alpha]_D^{20}$ +60° (c 0.5; pH 4.5 phosphate buffer); purity by HPLC 93.8%.

EXAMPLE 8

Cefuroxime

PCl$_5$ (3.160 g) and ethyl carbamate (1.566 g) were mixed and became a mobile oil on standing for ca 5 minutes (with brief ice-cooling). The oil was allowed to stand for 30 minutes at 23°, during which time all the PCl$_5$ dissolved. The oil was gradually heated to 80° over 3 hours, maintained at 80° for 1 hour and allowed to cool to ca 22°. The flask containing the reaction mixture was evacuated (ca 10 to 20 mm pressure) for a few minutes, dioxan (10 ml) was added, and the flask re-evacuated.

A solution of (6R,7R)-7-[Z-2-(fur-2-yl)-2-methoxyiminoacetamido]-3-hydroxymethylceph-3-em-4carboxylic acid (3.8 g) in dioxan (35 ml) was added to the above isocyanate reagent in one portion and the resulting solution was stirred at ca 22° for 7 minutes. The reaction mixture was poured into 3% aqueous NaHCO$_3$ solution (170 ml) and the pH was adjusted to 5 by the addition of more aqueous NaHCO$_3$ solution. After heating to 40° for 2 hours and allowing to cool to 22° over 14 hours, the reaction mixture was washed (at pH 5.9) with ethyl acetate (2×200 ml), the aqueous layer was separated, layered with ethyl acetate (200 ml), and acidified with concentrated hydrochloric acid to pH 1.9. The organic layer was separated and the aqueous layer re-extracted with ethyl acetate (200 ml). The organic extracts were combined, washed with brine (2×400 ml), dried (MgSO$_4$) and evaporated to give a white solid which, on trituration with ether (100 ml) afforded the title compound (3.18 g, 75% m.p. (M$_{SO}^2$) 175°; [α]$_D$+42° (c 1.02, DMSO).

The mother liquors yielded a further quantity of crude title compound (617 mg, 14%).

EXAMPLE 9

Cefuroxime

This reaction was carried out on the same scale as that described in Example 8 except that the ethyl carbamate was dissolved in dioxan (25 ml) and the PCl$_5$ was added under nitrogen at ca 25°. When dissolution was complete the reaction mixture was heated from 25° to ca 75° over 1.25 hours. The temperature was maintained at ca 75° for a further 45 minutes after which the solution was cooled to ca 10°, and evacuated at water-pump vacuum for 5 minutes at 5° to remove dissolved hydrogen chloride.

A solution of (6R,7R)-7-[Z-2-(fur-2-yl)-2-methoxyiminoacetamido]-3-hydroxymethyl-ceph-3-em-4-carboxylic acid (3.84 g) in dioxan (35 ml) was added to the above isocyanate solution at ca 25°. The reaction and work up was similar to that described in Example 8, except that the product was not triturated with ether, and yielded the title compound as a pale yellow solid, (3.28 g, 77%) m.p. (M$_{80}^2$)179°; [α]$_D^{22}$+54.4° (c.1.0, DMSO).

EXAMPLE 10

Cefuroxime Sodium

A solution of methyl carbamate (5.63 g) in dichloromethane (19 ml) was added over 12 minutes to a stirred suspension of PCl$_5$ (16.35 g) in dichloromethane (19 ml). The resulting solution was warmed gradually from 3° to reflux over 1.5 hours and then maintained at reflux for a further 4.5 hours, cooled to 20° and stored overnight. The dichloromethane was removed by distillation until the temperature of the residual dichlorophosphinyl isocyanate had risen to 110°. The isocyanate was cooled to ca. 25° and dissolved in THF (50 ml), and the resulting solution was cooled to −5°. A solution of (6R,7R)-7-[Z-2-(fur-2-yl)-2-methoxyiminoacetamido]-3-hydroxymethylceph-3-em-4-carboxylic acid (19.07 g) in THF (75 ml), precooled to below 5°, was added over 8 minutes keeping the temperature of the mixture in the range 0° to −5°. The resulting clear solution was stirred at 0° to −10° for 45 minutes and added to water (150 ml) at 24°. 25% Aqueous sodium hydroxide solution was added over 4 minutes to adjust the pH of the mixture to 3.0. The mixture was heated at 45° for 3 hours 20 minutes keeping the pH in the range 3.0 to 3.5 by the periodic addition of concentrated hydrochloric acid. Ethyl acetate (125 ml) was added and the reaction mixture was worked up as in Example 7, but using ethyl acetate as extracting solvent and a 20% solution of sodium 2-ethyl hexanoate in ethyl acetate to give the title compound (20.71 g, 89.5%) containing 2.7% water and 0.85% ethyl acetate; [α]$_D^{20}$−61° (c 0.5; pH 4.5 phosphate); λ$_{max}$ (H$_2$O) 273 nm (E$_{1\ cm}^{1\%}$ 387); purity by HPLC 93.4% and by TLC 93.5%.

EXAMPLE 11

Sodium (6R,7S)-3-Carbamoyloxymethyl-7-methoxy-7-phenylacetamidoceph-3-em-4-carboxylate A solution of dichlorophosphinylisocyanate (0.48 g) in THF (2 ml) was added to a cooled ca. 0° solution of (6R,7S)-3-hydroxymethyl-7-methoxy-7-phenylacetamidoceph3-em-4-carboxylic acid (0.757 g) in THF (5 ml).

After 7 minutes the reaction solution was poured into water (10 ml) and after 2 minutes pH 4 buffer (70 ml) was added. The pH had fallen to 1.5 and solid NaHCO$_3$ was added to give a pH of 4.

The solution was maintained at 43° for 3½ hours and then the pH was adjusted to 6.8 by addition of NaHCO$_3$. The solution was washed with ethyl acetate (35 ml).

The aqueous phase was adjusted to pH 2 by addition of orthophosphoric acid and the solution was extracted with ethyl acetate (2×50 ml).

The combined organic extracts were washed with saturated brine (2×50 ml), dried (MgSO$_4$) and evaporated in vacuo to an oil (0.800 g).

A solution of the above oil in acetone (8 ml) was treated with a solution of sodium 2-ethylhexanoate (0.316 g) in acetone.

The resulting suspension was refrigerated for 20 minutes and the product was filtered off and washed with cold acetone (15 ml) and stirred and washed with ether (15 ml). The solid was filtered off, the filter-bed was washed with ether (15 ml) and the product dried in vacuo to give the title compound (0.50 g), [α]$_D^{20}$+199.5° (c 0.985, pH 7 phosphate buffer 0.2 M), λ$_{max}$ 238.5 nm (E$_{1\ cm}^{1\%}$ 155) and 265 nm (E$_{1\ cm}^{1\%}$ 186).

EXAMPLE 12

Diphenylmethyl (6R,7R)-3-carbamoyloxymethyl-7-(D-5-benzoylamino-5-diphenylmethoxycarbonylpentanamido)ceph3-em-4-carboxylate A cooled (3°) solution of diphenylmethyl (6R,7R)-7-(D-5-benzoylamino-5-diphenylmethoxycarbonylpentanamido)-3-hydroxymethylceph-3-em-4-carboxylate (1.64 g) in THF (10 ml) was treated with a solution of dichlorophosphinylisocyanate (0.48 g) in THF (5 ml). The solution was stirred for 5 minutes then water (50 ml) was added. THF (30 ml) was added to give a homogeneous solution and the pH was raised from 1.5 to 3.6 using NaHCO$_3$ and 2 N-hydrochloric acid. The mixture was kept at 44° and more THF (15 ml) was added and a two-phase system resulted.

After 3 hours the phase were separated and the aqueous layer was extracted with ethyl acetate (2×50 ml). The combined organic layers were washed successively with saturated aqueous NaHCO$_3$ (50 ml) and saturated brine (50 ml) and the combined aqueous solutions were extracted with ethyl acetate (2×50 ml). The organic phases were combined, washed with saturated brine (50 ml) and dried (MgSO$_4$) and evaporated in vacuo to a paleyellow solid (1.59 g). A portion (1.48 g) of this material was crystallised from ethanol (80 ml) to give the title di-ester (1.022 g) as white crystals m.p. (M$_{125}^2$) 185.4°, [α]$_D^{20}$+29.2° (c, 1.01, DMSO), λ$_{max}$ (CHCl$_3$)259 nm (E$_{1\ cm}^{1\%}$ 104, 8 995).

EXAMPLE 13

(6R,7R)-3-carbamoyloxymethyl-7-[Z-2-(2-triphenylmethylaminothiazol-4-yl)-2-methoxyiminoacetamido]-ceph-3-em4-carboxylic acid

A solution of (6R,7R)-3-acetoxymethyl-7-[Z-2-(2-triphenylmethylaminothiazol-4-yl)-2-methoxyiminoacetamido]ceph-3-em-4-carboxylic acid (0.039 g) in 0.2 molar pH 7 phosphate buffer (40 ml) was stirred with cells of Rhodospiridium toruloides (CBS 349) at 22° for 3 hours.

The mixture was filtered through kieselguhr and the pad was washed with saturated brine (20 ml). The filtrate was washed with ethyl acetate (25 ml) cooled to 7° and acidified under ethyl acetate (25 ml) to pH 2 by the addition of orthophosphoric acid.

Filtration through kieselguhr clarified the mixture and the pad was washed with ethyl acetate (10 ml). The layers were separated and the aqueous layer was re-extracted with ethyl acetate (25 ml). The combined organic layers were washed with saturated brine (2×25 ml), dried (MgSO$_4$) and evaporated to dryness to give a solid (0.018 g). A solution of this material (0.018 g) in dry THF (2 ml) was treated with a solution of dichlorophosphinylisocyanate (0.032 g) in THF (1 ml). After 3 minutes phosphate buffer (pH 4, 12 ml) was added and the pH adjusted to 3.8 by addition of 2 N sodium hydroxide solution.

After 3½ hours at 45° the pH was adjusted to 7.5 by addition of saturated aqueous NaHCO$_3$ and the mixture was filtered through kieselguhr and washed with ethyl acetate (25 ml).

The pH was adjusted to 2.0 by the addition of orthophosphoric acid and the solution was extracted with ethyl acetate (2×25 ml). The combined organic extracts were washed with water (20 ml) and saturated brine (20 ml) and dried (MgSO$_4$) and evaporated to give the title compound (0.0059) which had a similar nmr spectrum (DMSO-d$_6$) and t.l.c. behaviour (R$_f$0.35 in chloroform:methanol:formic acid=90:16:4; pink colouration when sprayed with ninhydrin in n-butanol and heated) as an authentic specimen.

We claim:

1. In a process for the preparation of a 3-carbamoyloxymethyl cephalosporin of formula

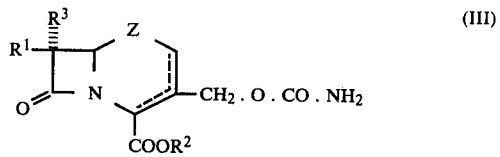

(wherein R$^1$ represents a C$_1$–C$_{40}$ protected amino group; R$^2$ represents a group selected from the group consisting of hydrogen atoms and carboxyl blocking groups; R$^3$ represents a group selected from the group consisting of hydrogen atoms and C$_1$–C$_8$ alkyl, C$_1$–C$_8$ alkylthio and C$_1$–C$_8$ alkoxy groups; Z is >S or >S→O (α- or β-); and the dotted line bridging the 2-, 3- and 4-positions of the molecule indicates that the compounds are ceph-2-em or ceph-3-em compounds) and, salts thereof, the steps which consist in contacting a 3-hydroxymethyl cephalosporin of formula

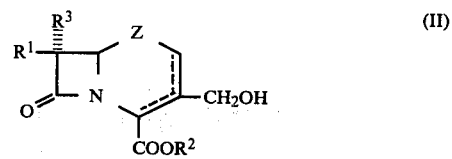

(wherein R$^1$, R$^2$, R$^3$, Z and the dotted line are as hereinbefore defined) with dichlorophosphinyl isocyanate and hydrolysing the resulting cephalosporin reaction product in at least one stage to the compound of formula (III).

2. The process of claim 1 wherein the hydrolysis is effected in a first stage at a pH of 10 or less and in a second stage at a pH below 5.

3. The process of claim 1 wherein the hydrolysis is effected in a single stage at a pH of 5 or less.

4. In a process for the preparation of (6R,7R)-3carbamoyloxymethyl-7-[Z-2-(fur-2-yl)-2-methoxyiminoacetamido]-ceph-3-em-4-carboxylic acid the steps which consist of contacting (6R,7R)-3-hydroxymethyl-[Z-2-(fur-2-yl)-2-methoxyiminoacetamido]-ceph-3-em-4-carboxylic acid with dichlorophosphinyl isocyanate and hydrolysing the resulting cephalosporin reaction product in at least one stage to the desired product.

* * * * *